United States Patent
Hahn et al.

(10) Patent No.: US 8,945,324 B2
(45) Date of Patent: Feb. 3, 2015

(54) PROCESS FOR MAKING ELASTOMERIC ABSORBENT GARMENTS TO REDUCE ABSORBENT BUNCHING

(75) Inventors: John T. Hahn, Merrill, WI (US); Julie Paveletzke, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 909 days.

(21) Appl. No.: 13/079,467

(22) Filed: Apr. 4, 2011

(65) Prior Publication Data
US 2012/0253310 A1    Oct. 4, 2012

(51) Int. Cl.
*A61F 13/15* (2006.01)
*A61F 13/494* (2006.01)
*A61F 13/496* (2006.01)

(52) U.S. Cl.
CPC .............. *A61F 13/494* (2013.01); *A61F 13/496* (2013.01); *A61F 13/15804* (2013.01)
USPC ............................ 156/163; 156/226; 156/229

(58) Field of Classification Search
None
See application file for complete search history.

(56) References Cited

U.S. PATENT DOCUMENTS

| | | |
|---|---|---|
| 2,568,595 A | 9/1951 | Rohrer |
| 3,488,778 A | 1/1970 | Goujon et al. |
| 3,828,367 A | 8/1974 | Bourgeois |
| 4,302,853 A | 12/1981 | Mesek |
| 4,515,595 A | 5/1985 | Kievit et al. |
| 4,595,441 A | 6/1986 | Holvoet et al. |
| 4,608,115 A | 8/1986 | Schroth et al. |
| 4,612,674 A | 9/1986 | Hashimoto |
| 4,641,381 A | 2/1987 | Heran et al. |
| 4,646,362 A | 3/1987 | Heran et al. |
| 4,652,487 A | 3/1987 | Morman |
| 4,655,760 A | 4/1987 | Morman et al. |
| 4,657,802 A | 4/1987 | Morman |
| 4,663,106 A | 5/1987 | Pomplun et al. |
| 4,663,220 A | 5/1987 | Wisneski et al. |
| 4,707,398 A | 11/1987 | Boggs |
| 4,720,415 A | 1/1988 | Vander Wielen et al. |
| 4,724,184 A | 2/1988 | Killian et al. |

(Continued)

FOREIGN PATENT DOCUMENTS

| | | |
|---|---|---|
| EP | 0 048 011 A1 | 3/1982 |
| EP | 0 449 271 A1 | 10/1991 |

(Continued)

OTHER PUBLICATIONS

American Society for Testing Materials (ASTM) Designation: D 882-95a, "Standard Test Method for Tensile Properties of Thin Plastic Sheeting," pp. 182-187, published Dec. 1995.

(Continued)

*Primary Examiner* — Barbara J Musser
(74) *Attorney, Agent, or Firm* — Kimberly-Clark Worldwide, Inc.

(57) ABSTRACT

A method of making disposable absorbent garments includes providing an elastomeric body panel and an absorbent assembly having an absorbent core. The method includes stretching the elastomeric body panel in the transverse direction, attaching side margins of the absorbent assembly to the stretched elastomeric body panel at attachment regions, and relaxing the body panel so as to induce folds in the absorbent assembly. A center region of the absorbent assembly between the attachment regions is minimally attached to the stretched elastomeric body panel to reduce bunching of the absorbent core. A garment made thereby is also disclosed.

6 Claims, 12 Drawing Sheets

(56) References Cited

U.S. PATENT DOCUMENTS

| | | |
|---|---|---|
| 4,726,807 A | 2/1988 | Young et al. |
| 4,756,709 A | 7/1988 | Stevens |
| 4,760,764 A | 8/1988 | De Jonckheere et al. |
| 4,764,234 A | 8/1988 | Smits et al. |
| 4,764,242 A | 8/1988 | Gressick et al. |
| 4,781,966 A | 11/1988 | Taylor |
| 4,789,699 A | 12/1988 | Kieffer et al. |
| 4,795,451 A | 1/1989 | Buckley |
| 4,804,379 A | 2/1989 | Toth et al. |
| 4,808,176 A | 2/1989 | Kielpikowski |
| 4,834,738 A | 5/1989 | Kielpikowski et al. |
| 4,863,779 A | 9/1989 | Daponte |
| 4,906,243 A | 3/1990 | Dravland |
| 4,938,753 A | 7/1990 | Van Gompel et al. |
| 4,940,464 A | 7/1990 | Van Gompel et al. |
| 4,965,122 A | 10/1990 | Morman |
| 4,981,747 A | 1/1991 | Morman |
| 5,098,419 A | 3/1992 | Gold |
| 5,114,781 A | 5/1992 | Morman |
| 5,116,662 A | 5/1992 | Morman |
| 5,147,343 A | 9/1992 | Kellenberger |
| 5,151,092 A | 9/1992 | Buell et al. |
| 5,163,932 A | 11/1992 | Nomura et al. |
| 5,169,706 A | 12/1992 | Collier, IV et al. |
| 5,171,236 A | 12/1992 | Dreier et al. |
| 5,171,239 A | 12/1992 | Igaue et al. |
| 5,188,627 A | 2/1993 | Igaue et al. |
| 5,226,992 A | 7/1993 | Morman |
| 5,236,430 A | 8/1993 | Bridges |
| 5,246,433 A | 9/1993 | Hasse et al. |
| 5,260,126 A | 11/1993 | Collier, IV et al. |
| 5,288,791 A | 2/1994 | Collier, IV et al. |
| 5,330,598 A | 7/1994 | Erdman et al. |
| 5,336,545 A | 8/1994 | Morman |
| 5,366,793 A | 11/1994 | Fitts, Jr. et al. |
| D354,132 S | 1/1995 | Minor |
| 5,385,775 A | 1/1995 | Wright |
| 5,399,219 A | 3/1995 | Roessler et al. |
| 5,414,470 A | 5/1995 | Hotta et al. |
| 5,464,401 A | 11/1995 | Hasse et al. |
| 5,496,429 A | 3/1996 | Hasse et al. |
| 5,503,908 A | 4/1996 | Faass |
| 5,564,543 A | 10/1996 | Wilson |
| 5,569,234 A | 10/1996 | Buell et al. |
| 5,575,783 A | 11/1996 | Clear et al. |
| 5,593,400 A | 1/1997 | O'Leary |
| 5,599,417 A | 2/1997 | Glaug et al. |
| 5,601,542 A | 2/1997 | Melius et al. |
| 5,611,790 A | 3/1997 | Osborn, III et al. |
| 5,649,919 A | 7/1997 | Roessler et al. |
| 5,651,862 A | 7/1997 | Anderson et al. |
| 5,685,874 A | 11/1997 | Buell et al. |
| 5,695,846 A | 12/1997 | Lange et al. |
| 5,716,351 A | 2/1998 | Roe et al. |
| 5,735,839 A | 4/1998 | Kawaguchi et al. |
| 5,746,730 A | 5/1998 | Suzuki et al. |
| 5,746,731 A | 5/1998 | Hisada |
| 5,749,865 A | 5/1998 | Yamamoto et al. |
| 5,759,340 A | 6/1998 | Boothe et al. |
| 5,761,478 A | 6/1998 | Chen et al. |
| 5,769,838 A | 6/1998 | Buell et al. |
| 5,782,819 A | 7/1998 | Tanzer et al. |
| 5,807,368 A | 9/1998 | Helmer |
| 5,817,086 A | 10/1998 | Kling |
| 5,827,259 A | 10/1998 | Laux et al. |
| 5,846,232 A | 12/1998 | Serbiak et al. |
| 5,858,013 A | 1/1999 | Kling |
| 5,858,151 A | 1/1999 | Igaue et al. |
| 5,904,675 A | 5/1999 | Laux et al. |
| 5,906,603 A | 5/1999 | Roe et al. |
| 5,932,497 A | 8/1999 | Morman et al. |
| 5,947,948 A | 9/1999 | Roe et al. |
| 6,010,586 A | 1/2000 | Suprise |
| 6,015,935 A | 1/2000 | Lavon et al. |
| 6,049,023 A | 4/2000 | Blenke et al. |
| 6,099,516 A | 8/2000 | Pozniak et al. |
| 6,113,717 A | 9/2000 | Vogt et al. |
| 6,120,487 A | 9/2000 | Ashton |
| 6,132,410 A | 10/2000 | Van Gompel et al. |
| 6,139,004 A | 10/2000 | Couillard et al. |
| 6,149,637 A | 11/2000 | Allen et al. |
| 6,171,432 B1 | 1/2001 | Brisebois et al. |
| 6,187,425 B1 | 2/2001 | Bell et al. |
| 6,193,701 B1 | 2/2001 | Van Gompel et al. |
| 6,217,563 B1 | 4/2001 | Van Gompel et al. |
| 6,217,692 B1 | 4/2001 | Kling |
| 6,258,077 B1 | 7/2001 | Buell et al. |
| 6,264,641 B1 | 7/2001 | Van Gompel et al. |
| 6,264,643 B1 | 7/2001 | Toyoda |
| 6,264,784 B1 | 7/2001 | Menard et al. |
| 6,302,871 B1 | 10/2001 | Nakao et al. |
| 6,306,122 B1 | 10/2001 | Narawa et al. |
| 6,323,389 B1 | 11/2001 | Thomas et al. |
| 6,325,787 B1 | 12/2001 | Roe et al. |
| 6,336,922 B1 | 1/2002 | Vangompel et al. |
| 6,352,528 B1 | 3/2002 | Weber et al. |
| 6,359,192 B1 | 3/2002 | Schmidt et al. |
| 6,364,863 B1 | 4/2002 | Yamamoto et al. |
| 6,367,089 B2 | 4/2002 | Van Gompel et al. |
| 6,375,646 B1 | 4/2002 | Widlund et al. |
| 6,387,471 B1 | 5/2002 | Taylor et al. |
| 6,478,786 B1 | 11/2002 | Glaug et al. |
| 6,514,233 B1 | 2/2003 | Glaug |
| 6,607,515 B2 | 8/2003 | Glaug et al. |
| 6,827,804 B2 | 12/2004 | Otsubo et al. |
| 6,960,197 B1 | 11/2005 | Gustafsson et al. |
| 6,979,308 B1 | 12/2005 | MacDonald et al. |
| 6,979,380 B2 | 12/2005 | Thorson et al. |
| 7,011,653 B2 | 3/2006 | Imsangjan et al. |
| 7,201,744 B2 | 4/2007 | Van Gompel et al. |
| 2001/0025164 A1 | 9/2001 | Krautkramer et al. |
| 2001/0025165 A1 | 9/2001 | Shimoe |
| 2001/0047159 A1 | 11/2001 | Mizutani |
| 2002/0002021 A1 | 1/2002 | May et al. |
| 2002/0009940 A1 | 1/2002 | May et al. |
| 2002/0010450 A1 | 1/2002 | Suzuki et al. |
| 2002/0072728 A1 | 6/2002 | Shinohara et al. |
| 2002/0086602 A1 | 7/2002 | Friderich et al. |
| 2002/0104608 A1 | 8/2002 | Welch et al. |
| 2002/0151864 A1 | 10/2002 | Otsubo et al. |
| 2002/0165516 A1 | 11/2002 | Datta et al. |
| 2003/0088230 A1 | 5/2003 | Balogh et al. |
| 2003/0121614 A1 | 7/2003 | Tabor et al. |
| 2003/0144643 A1 | 7/2003 | Jarpenberg et al. |
| 2003/0217447 A1 | 11/2003 | Widlund |
| 2004/0060649 A1 | 4/2004 | Van Gompel et al. |
| 2004/0060678 A1 | 4/2004 | Eriksson et al. |
| 2004/0064121 A1 | 4/2004 | Van Gompel et al. |
| 2004/0078018 A1 | 4/2004 | Gompel et al. |
| 2004/0122405 A1 | 6/2004 | Van Gompel et al. |
| 2005/0010188 A1 | 1/2005 | Glaug et al. |
| 2005/0143710 A1* | 6/2005 | Van Gompel et al. ........ 604/393 |
| 2006/0116655 A1 | 6/2006 | Gompel et al. |
| 2009/0194218 A1 | 8/2009 | Torstensson et al. |
| 2009/0292266 A1 | 11/2009 | Back |
| 2011/0030886 A1 | 2/2011 | Van Gompel et al. |

FOREIGN PATENT DOCUMENTS

| | | |
|---|---|---|
| EP | 0 753 292 A2 | 1/1997 |
| EP | 0 794 751 B1 | 6/1999 |
| EP | 1 108 372 A1 | 6/2001 |
| EP | 1 155 668 A2 | 11/2001 |
| EP | 0 907 510 B1 | 3/2002 |
| EP | 1 240 881 A2 | 9/2002 |
| EP | 1 249 214 A2 | 10/2002 |
| EP | 1 366 735 A1 | 12/2003 |
| EP | 1 428 487 A1 | 6/2004 |
| EP | 1 574 193 A1 | 9/2005 |
| FR | 2 644 694 A1 | 9/1990 |
| JP | 03-176053 A | 7/1991 |
| JP | 2001-029389 A | 2/2001 |
| WO | WO 93/17648 A1 | 9/1993 |
| WO | WO 98/29251 A1 | 7/1998 |

(56) References Cited

FOREIGN PATENT DOCUMENTS

| | | |
|---|---|---|
| WO | WO 99/56688 A1 | 11/1999 |
| WO | WO 00/37010 A1 | 6/2000 |
| WO | WO 00/39201 A2 | 7/2000 |
| WO | WO 00/47152 A1 | 8/2000 |
| WO | WO 01/87588 A2 | 11/2001 |
| WO | WO 01/87589 A2 | 11/2001 |
| WO | WO 01/88245 A2 | 11/2001 |
| WO | WO 02/24131 A1 | 3/2002 |
| WO | WO 2004/030477 A1 | 4/2004 |
| WO | WO 2004/060238 A1 | 7/2004 |
| WO | WO 2005/007051 A1 | 1/2005 |

OTHER PUBLICATIONS

Federal Test Method Standard (FTMS) No. 191A, Method 5514, "Water Resistance of Cloth; Low Range, Hydrostatic Pressure Method," Jul. 20, 1978, 3 pages.

* cited by examiner

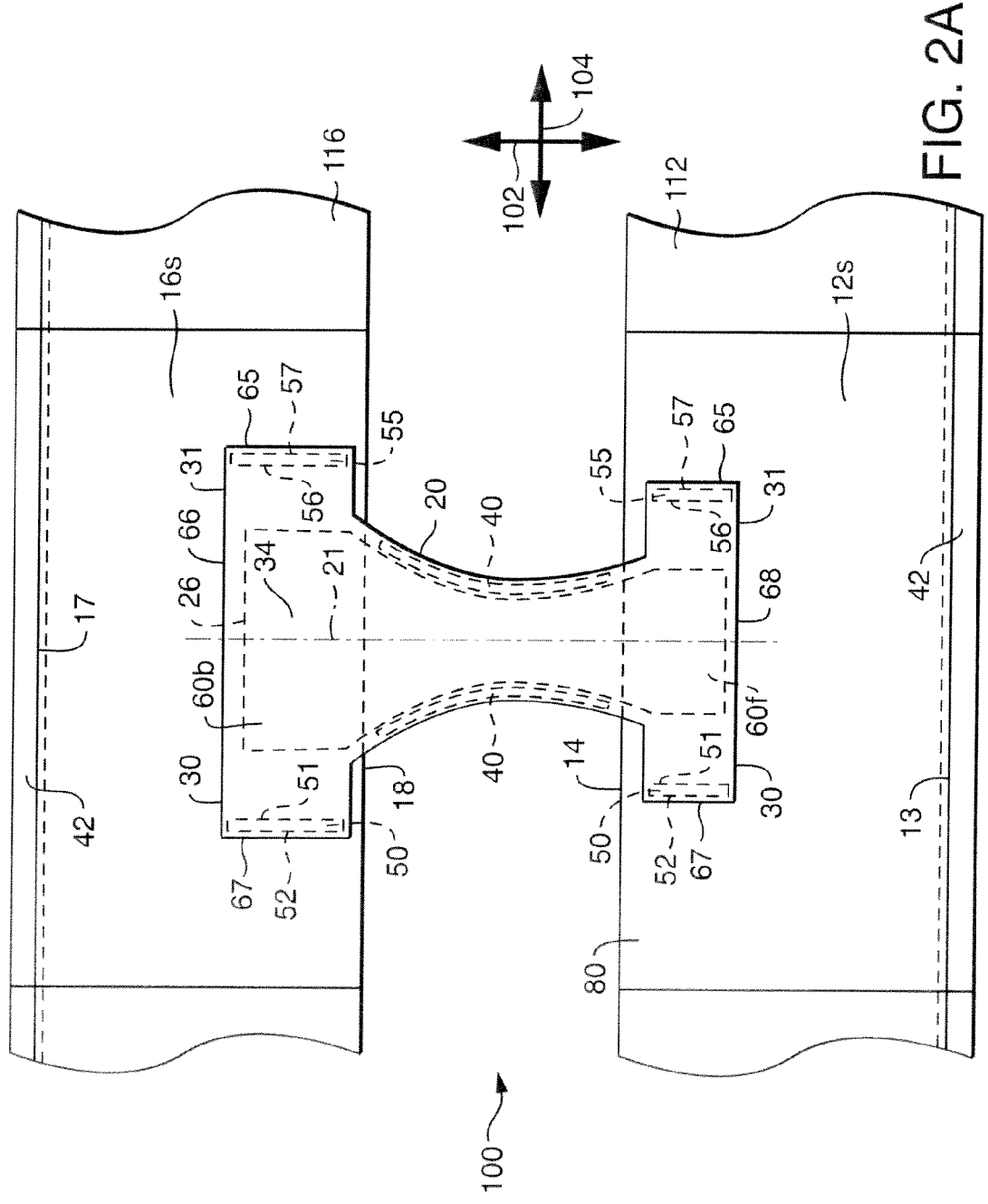

PROCESS FOR MAKING ELASTOMERIC ABSORBENT GARMENTS TO REDUCE ABSORBENT BUNCHING

BACKGROUND

People rely on disposable absorbent products in their everyday lives, including such articles as adult incontinence products, enuresis pants, training pants, and diapers. Many manufacturers seek to better meet the needs of users of such products. For example, there is a need to further improve fit, discretion, and leakage protection for many products.

Some products employ elasticization across the front and/or back of the garment to assist in keeping the product fit snugly against the wearer. Some products employ a multiplicity of elastic strands within front and/or back waist panels to provide the elasticization, while other products employ elastomeric polymeric films, often sandwiched with one or more nonwoven layers. Most products also include an absorbent member, constructed from wood pulp fluff, superabsorbent polymers, or other absorbent material to absorb fluids such as urine. The absorbent member is typically positioned in the crotch region and extends forward and backward into the front and/or back regions of the product. In certain prior art products, some of the elastic members that extend across the front and/or back waist panels overlap the absorbent member at various locations, by virtue of the absorbent member extending forward/backward into the front/back waist regions. This can be undesirable, because the tension of the elastic members can tend to gather the absorbent member, or cause it to "bunch." Such bunching of the absorbent member can create fit and discretion problems. From a fit standpoint, a bunched absorbent is less likely to lie snugly against the body, potentially increasing the incidence of leakage. From a discretion standpoint, excessive bunching tends to make the product more bulky and therefore more visible under clothing. This circumstance is particularly problematic for incontinence articles, such as enuresis pants and adult pull-on style disposable absorbent underwear, as the wearers of such products generally are embarrassed about their condition and wish to employ protection which is as discreet as possible.

In certain conventional processes to manufacture disposable absorbent pants having elasticization, an absorbent composite (such as a pulp fluff/superabsorbent matt sandwiched between polymeric film and/or nonwoven layers) is affixed to one or more elastomeric panels designed to form part of the pant and to fit snugly against the body. These elastomeric panels are provided in continuous web form and may be introduced into the manufacturing process in a stretched state. Each absorbent composite is attached to the continuous web of elastomeric material. Upon completion of the manufacturing steps (after the absorbent composite has been attached), the elastomeric material is allowed to contract. This contraction can cause the absorbent composite to bunch and gather, which is undesirable as explained above.

Therefore, there remains a need for a process for producing absorbent garments having elasticized panels that are less likely to cause undesirable gathering and bunching of the absorbent member.

SUMMARY OF THE INVENTION

In response to the above described unmet needs in the art, a new method for manufacturing elastomeric disposable absorbent garments, and garments made thereby, have been invented.

In one aspect, the present invention is directed to a method of making a disposable absorbent garment. The method defines a longitudinal direction and a transverse direction perpendicular to the longitudinal direction. The method comprises providing an elastomeric body panel that defines a waist edge and a crotch edge longitudinally opposite the waist edge; providing an absorbent assembly that defines transversely opposed first and second assembly side edges and that defines longitudinally opposed first and second assembly end edges, the absorbent assembly comprising an absorbent core, the absorbent core having transversely opposed first and second core side edges, the absorbent assembly further comprising a first side margin that extends transversely outward from the first core side edge to the first assembly side edge, the absorbent assembly further comprising a second side margin that extends transversely outward from the second core side edge to the second assembly side edge; stretching the elastomeric body panel in the transverse direction to define a stretched elastomeric body panel; superposing the absorbent assembly over the elastomeric body panel; attaching the first side margin to the stretched elastomeric body panel along a first attachment region, the first attachment region extending generally in the longitudinal direction, the first attachment region defining a longitudinally extending first edge and a longitudinally extending second edge disposed transversely outward from the longitudinally extending first edge, wherein the first edge of the first attachment region is disposed transversely outward from the first core side edge; attaching the second side margin to the stretched elastomeric body panel along a second attachment region, the second attachment region extending generally in the longitudinal direction, the second attachment region defining a longitudinally extending first edge and a longitudinally extending second edge disposed transversely outward from the longitudinally extending first edge, wherein the first edge of the second attachment region is disposed transversely outward from the second core side edge; the absorbent assembly further defining a center region that extends transversely from the first edge of the first attachment region to the first edge of the second attachment region and that extends longitudinally from the first assembly end edge to the crotch edge, wherein said center region of the absorbent assembly is minimally attached to the stretched elastomeric body panel; relaxing the elastomeric body panel to define a relaxed elastomeric body panel; transversely folding the first side margin to create at least two longitudinally extending fold lines in the first side margin; and transversely folding the second side margin to create at least two longitudinally extending fold lines in the second side margin.

In particular embodiments of the method aspect, transversely folding the first side margin imparts a z-folded cross section to the first side margin, and transversely folding the second side margin imparts a z-folded cross section to the second side margin.

In particular embodiments, the method further comprises attaching at least 2% and at most 25% of the area of the center region of the absorbent assembly to the stretched elastomeric body panel.

In particular embodiments, the method further comprises attaching the center region of the absorbent assembly to the stretched elastomeric body panel along a middle attachment region, the middle attachment region extending generally in the longitudinal direction, wherein a transverse centerline of the middle attachment region is positioned approximately midway between the first assembly side edge and the second assembly side edge.

In particular embodiments, the method further comprises attaching the center region of the absorbent assembly to the stretched elastomeric body panel along a top attachment region, the top attachment region extending generally in the transverse direction along the first assembly end edge.

In particular embodiments of the method aspect, the entire area of the center region is unattached to the stretched elastomeric body panel.

In another aspect, the present invention is direct to a disposable absorbent garment. The garment defines a longitudinal direction and a transverse direction perpendicular to the longitudinal direction. The garment comprises an elastomeric body panel that defines a waist edge and a crotch edge longitudinally opposite the waist edge; an absorbent assembly that defines transversely opposed first and second assembly side edges and that defines longitudinally opposed first and second assembly end edges, the absorbent assembly comprising an absorbent core, the absorbent core having transversely opposed first and second core side edges, the absorbent assembly further comprising a first side margin that extends transversely outward from the first core side edge to the first assembly side edge, the absorbent assembly further comprising a second side margin that extends transversely outward from the second core side edge to the second assembly side edge. The absorbent assembly is at least partially superposed over the elastomeric body panel. The first side margin is attached to the elastomeric body panel along a first attachment region, the first attachment region extending generally in the longitudinal direction, the first attachment region defining a longitudinally extending first edge and a longitudinally extending second edge disposed transversely outward from the longitudinally extending first edge, and the first edge of the first attachment region is disposed transversely outward from the first core side edge. The second side margin is attached to the elastomeric body panel along a second attachment region, the second attachment region extending generally in the longitudinal direction, the second attachment region defining a longitudinally extending first edge and a longitudinally extending second edge disposed transversely outward from the longitudinally extending first edge, and the first edge of the second attachment region is disposed transversely outward from the second core side edge. The absorbent assembly further defines a center region that extends transversely from the first edge of the first attachment region to the first edge of the second attachment region and that extends longitudinally from the first assembly end edge to the crotch edge, and the center region of the absorbent assembly is minimally attached to the elastomeric body panel. The first side margin defines at least two longitudinally extending fold lines, and the second side margin defines at least two longitudinally extending fold lines.

In particular embodiments of the garment, the first side margin define a z-folded cross section and the second side margin defines a z-folded cross section.

In particular embodiments of the garment, at least 2% and at most 25% of the area of the center region of the absorbent assembly is attached to the elastomeric body panel.

In particular embodiments of the garment, the center region of the absorbent assembly is attached to the elastomeric body panel along a middle attachment region, the middle attachment region extending generally in the longitudinal direction, and a transverse centerline of the middle attachment region is positioned approximately midway between the first assembly side edge and the second assembly side edge.

In particular embodiments of the garment, the center region of the absorbent assembly is attached to the stretched elastomeric body panel along a top attachment region, the top attachment region extending generally in the transverse direction along the first assembly end edge.

In particular embodiments of the garment, the entire area of the center region is unattached to the stretched elastomeric body panel.

BRIEF DESCRIPTION OF THE DRAWINGS

FIG. 2A representatively illustrates a plan view of one variant of a section of the manufacturing process of FIG. 1.

DEFINITIONS

Figure 1:
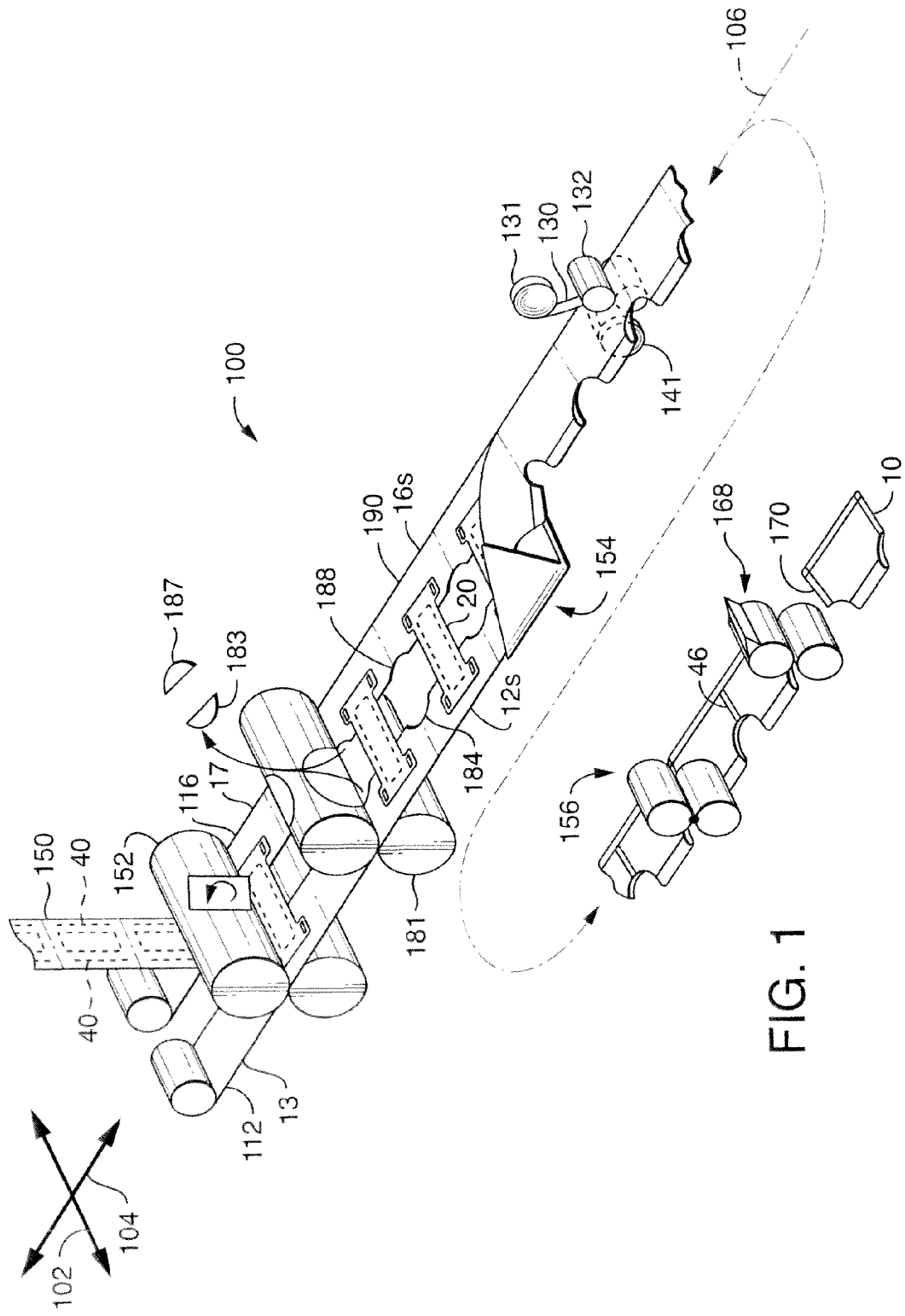
FIG. 1 representatively illustrates a perspective view of one embodiment of a manufacturing process incorporating principles of the method aspect of the present invention.

Within the context of this specification, each term or phrase below will include the following meaning or meanings. Additional terms are defined elsewhere in the specification.

"Attached" refers to the joining, adhering, bonding, connecting, or the like, of two elements. Two elements will be considered to be attached together when they are attached directly to one another or indirectly to one another, such as when each is directly attached to intermediate elements.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Integral" is used to refer to various portions of a single unitary element rather than separate structures bonded to or placed with or placed near one another.

"Layer" when used in the singular can have the dual meaning of a single element or a plurality of elements.

These terms may be defined with additional language in the remaining portions of the specification.

DETAILED DESCRIPTION OF PARTICULAR EMBODIMENTS

Reference to FIGS. 1-11 shall be made in describing various aspects and embodiments of the invention. It should be noted that the embodiments depicted in FIGS. 1-11 are merely representative examples of the garment and process aspects of the invention. Although for illustrative purposes certain features of the present invention shall be described and illustrated with respect to an adult incontinence garment and process for making such garment, the various aspects and embodiments of the present invention are also suitable for use with disposable diapers, disposable swim pants, disposable training pants, disposable enuresis garments, and the like. As representatively illustrated in FIGS. 1-3, the invention in one aspect is directed to a method 100 of making a disposable absorbent garment 10. The method defines a longitudinal direction 102 and a transverse direction 104 which is perpendicular to the longitudinal direction 102. In particular embodiments of the method, such as that representatively illustrated in FIGS. 1-3, the transverse direction 104 is parallel to a machine direction, and the longitudinal direction 102 is parallel to a cross-machine direction.

The method 100 comprises providing at least one elastomeric body panel, such as a front elastomeric body panel 12, that defines a front waist edge 13 and a front crotch edge 14 longitudinally opposite the waist edge 13. The elastomeric body panel 12 is preferably provided as a part of a continuous web 112 of interconnected elastomeric body panels 12. Particular embodiments can further include a back elastomeric body panel 16 that defines a back waist edge 17 and a back crotch edge 18. The elastomeric body panel 16 is preferably provided as a part of a continuous web 116 of interconnected elastomeric body panels 16. Each elastomeric body panel defines an inner, body-facing surface 80 and an opposite, garment-facing surface 81.

The method 100 further comprises providing an absorbent assembly 20 (such as via a supply 150 of individual absorbent assemblies 20) that defines transversely opposed first and second absorbent assembly side edges 65, 67 and that defines longitudinally opposed first and second absorbent assembly end edges 66, 68. The absorbent assembly 20 comprises an absorbent core 26. The absorbent core 26 defines transversely opposed first and second core side edges 28, 29. The absorbent assembly 20 includes a first side margin 30 that extends transversely outward from the first core side edge 28 to the first assembly side edge 65. The absorbent assembly 20 further includes a second side margin 31 that extends transversely outward from the second core side edge 29 to the second assembly side edge 67. "Transversely outward" as used herein means in a direction away from a transversely central, longitudinally extending imaginary axis 21 of the absorbent assembly 20.

Figure 4:
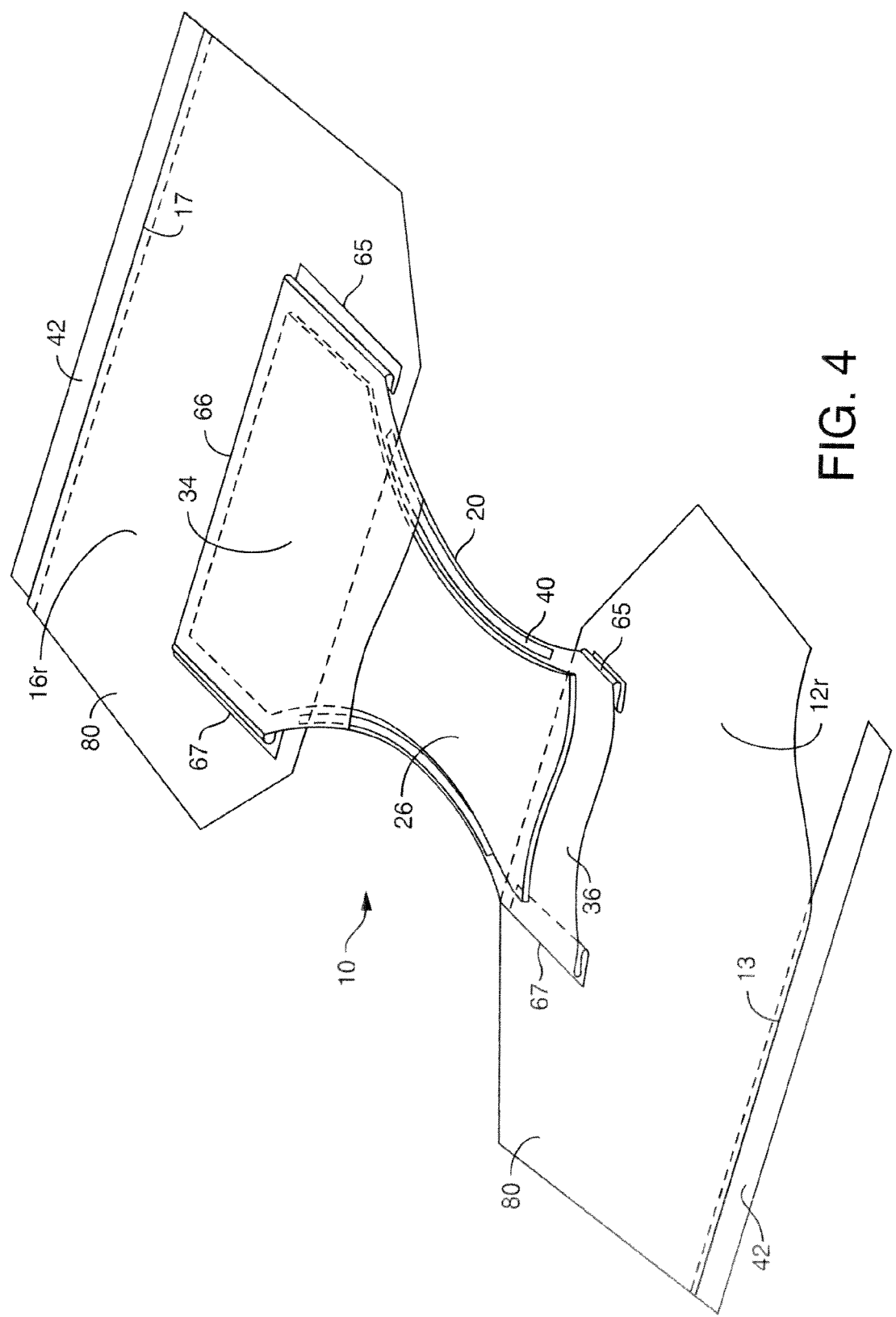
FIG. 4 representatively illustrates a perspective view of a disposable absorbent garment incorporating principles of the garment aspect of the present invention, shown in a relaxed and laid-flat condition, prior to the joining of the front and back waist regions, and showing the surface of the article that faces toward the wearer when the article is worn.
Figure 5:
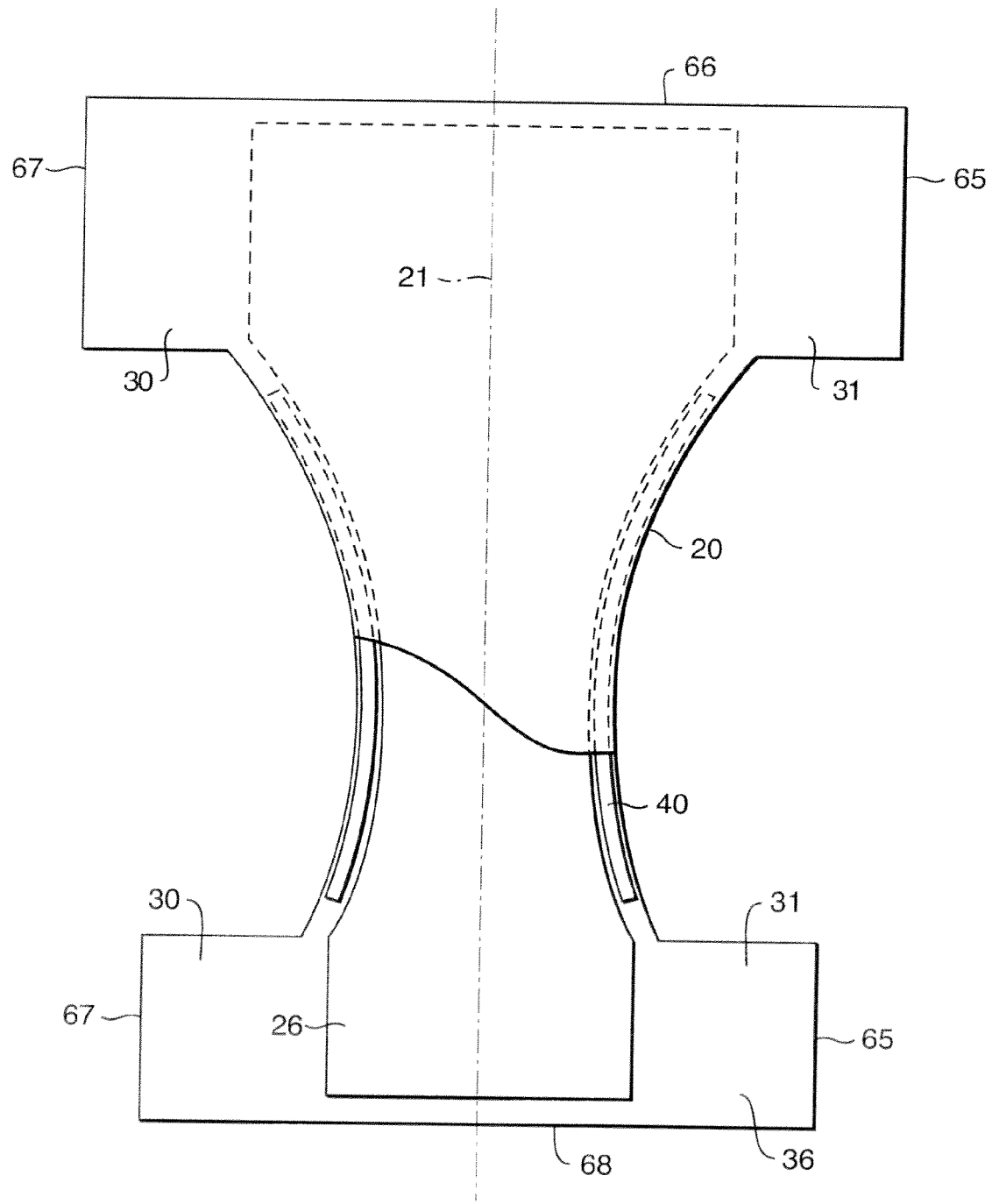
FIG. 5 representatively illustrates an absorbent assembly suitable for use in conjunction with the method and garment aspects of the present invention.
Figure 6:
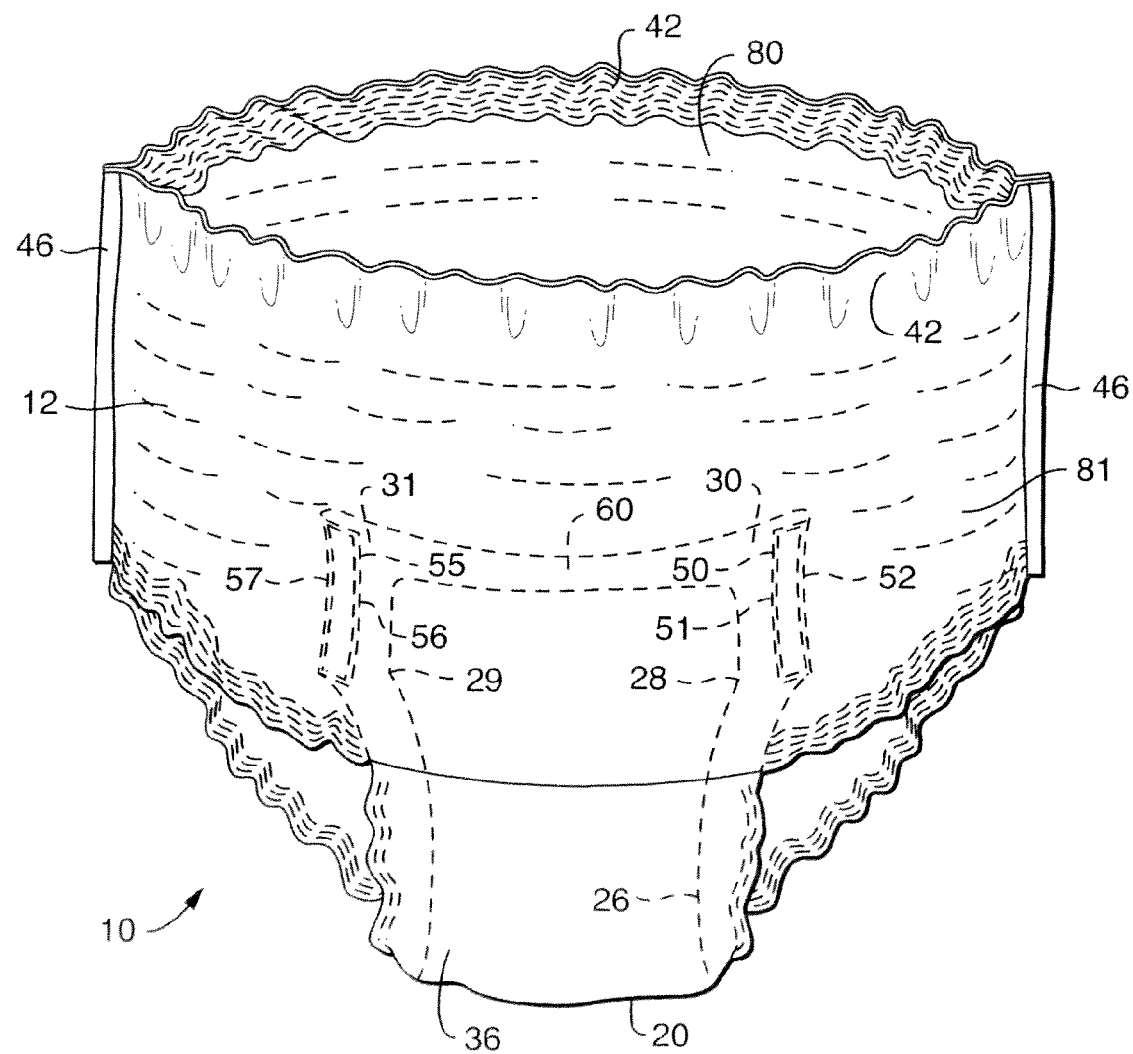
FIG. 6 representatively illustrates a front perspective view of a garment incorporating principles of the garment aspect of the present invention, shown in a fully assembled condition.
Figure 7:
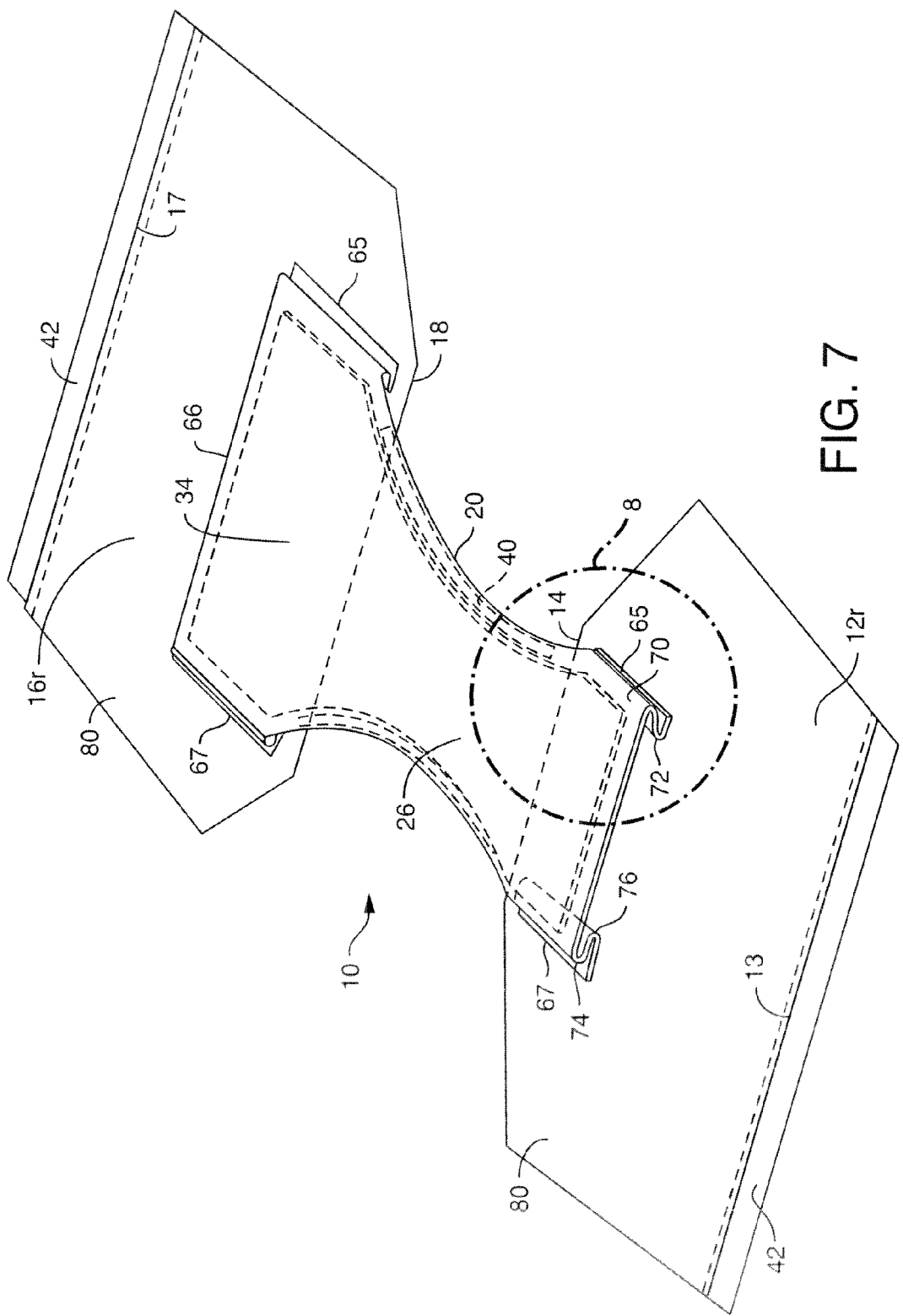
FIG. 7 representatively illustrates a perspective view of a disposable absorbent garment incorporating principles of the garment aspect of the present invention, shown in a relaxed and laid-flat condition, prior to the joining of the front and back waist regions, and showing the surface of the article that faces toward the wearer when the article is worn.
Figure 8:
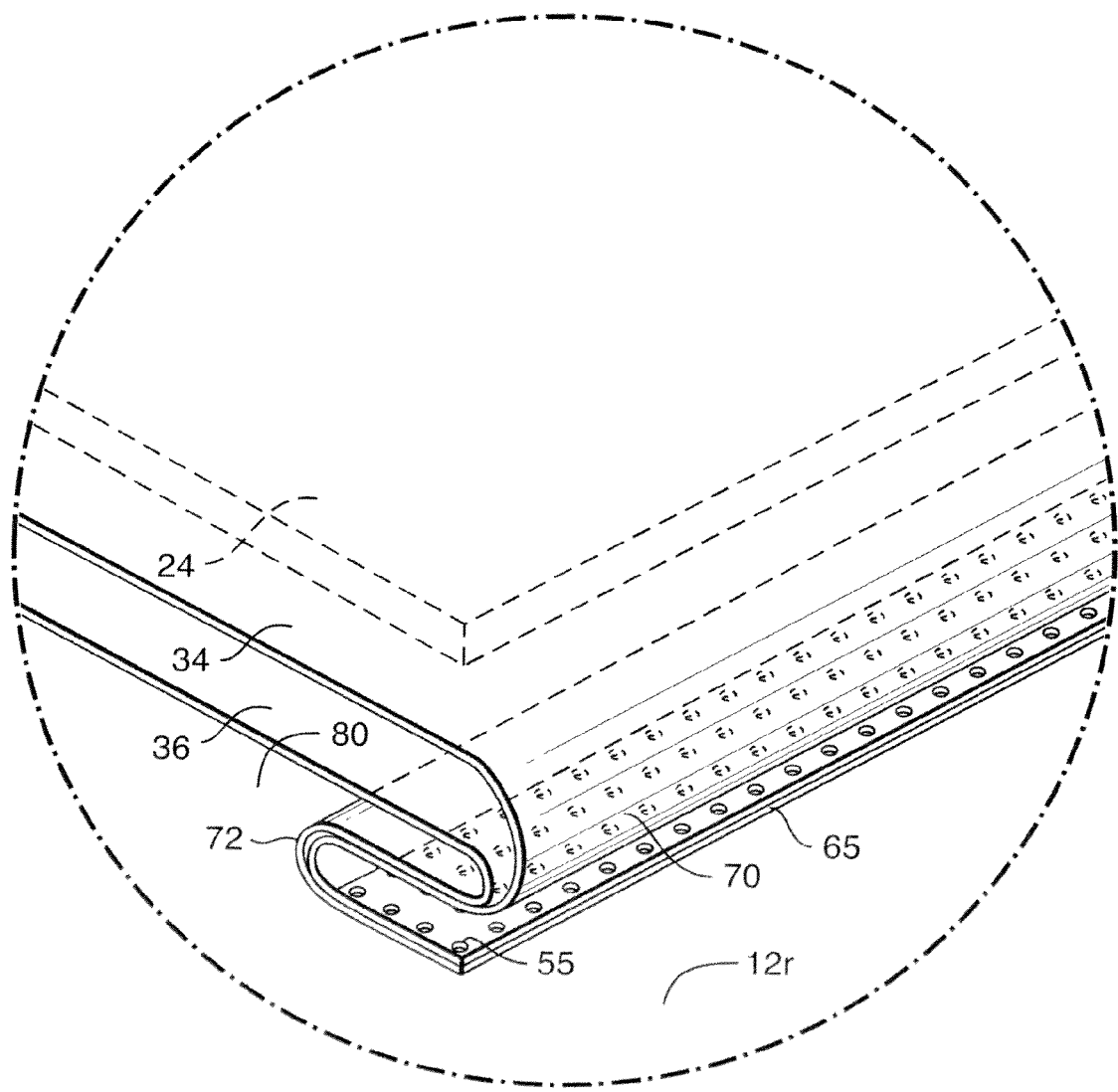
FIG. 8 is a magnified perspective view of a section of the garment representatively illustrated in FIG. 7.
Figure 9:
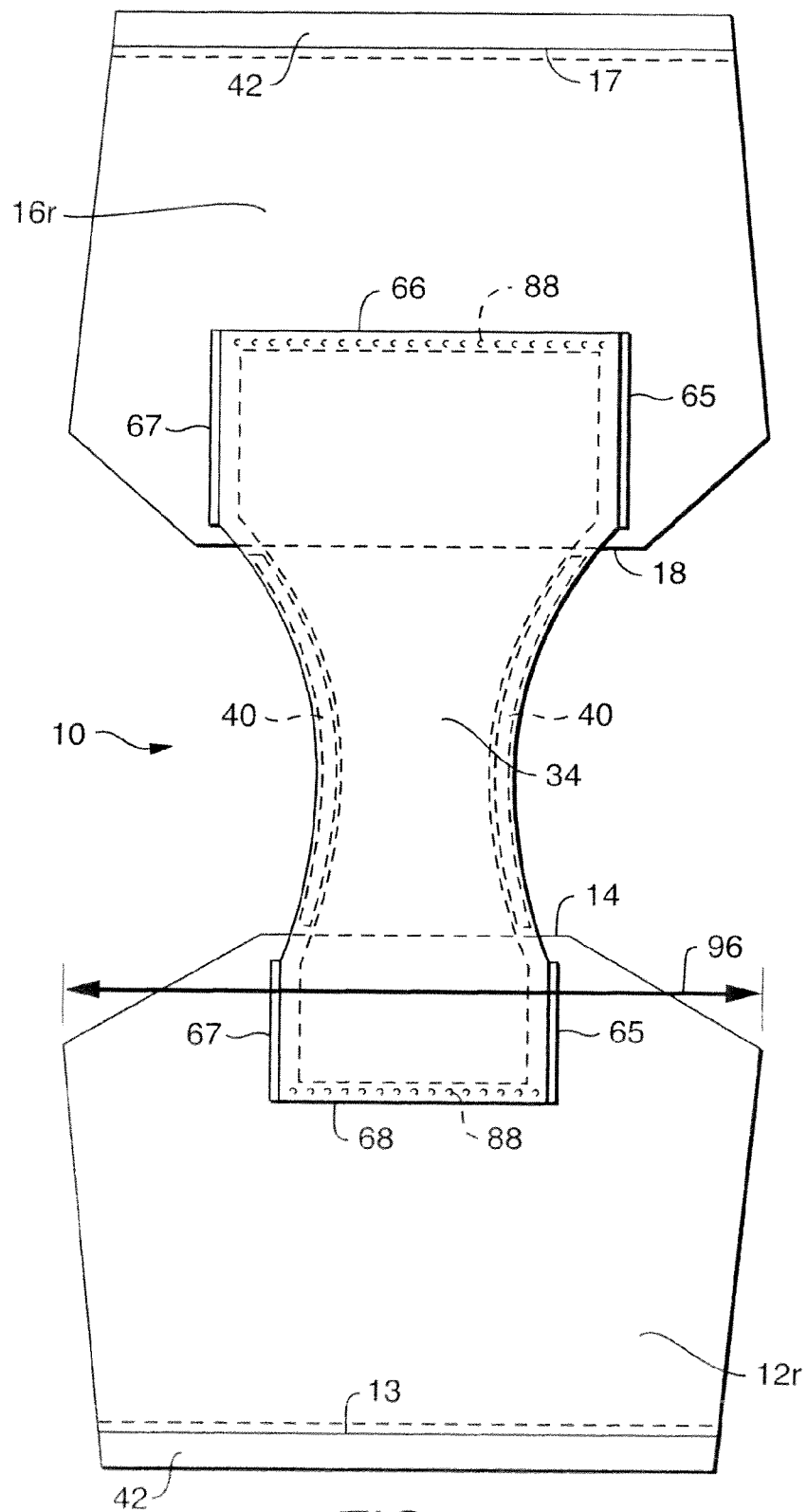
FIG. 9 representatively illustrates a plan view of one embodiment of a disposable absorbent garment incorporating principles of the garment aspect of the present invention, shown in a relaxed and laid-flat condition, prior to the joining of the front and back waist regions, and showing the surface of the article that faces toward the wearer when the article is worn.
Figure 10:
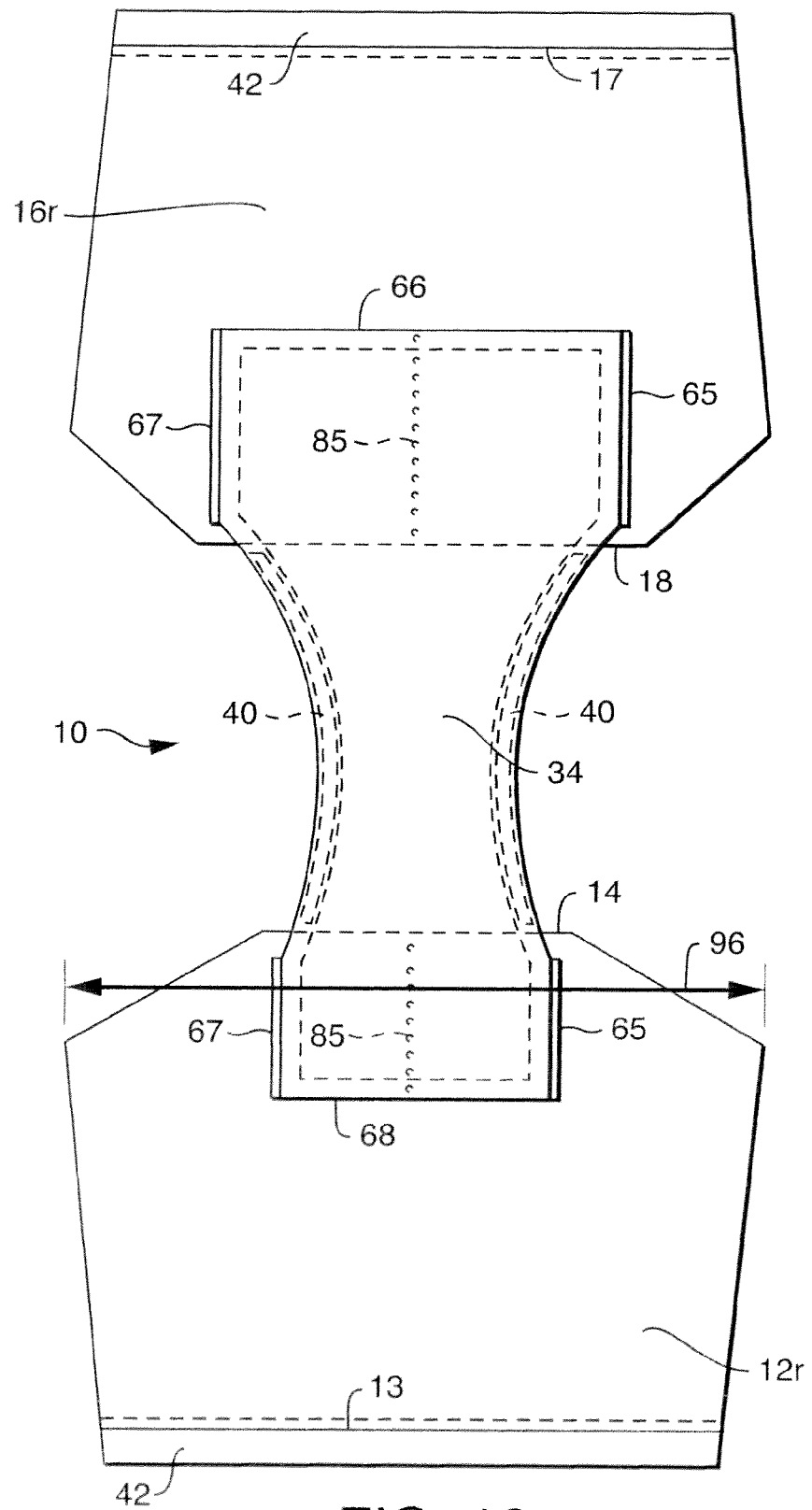
FIG. 10 representatively illustrates a plan view of another embodiment of a disposable absorbent garment incorporating principles of the garment aspect of the present invention, shown in a relaxed and laid-flat condition, prior to the joining of the front and back waist regions, and showing the surface of the article that faces toward the wearer when the article is worn.
Figure 11:
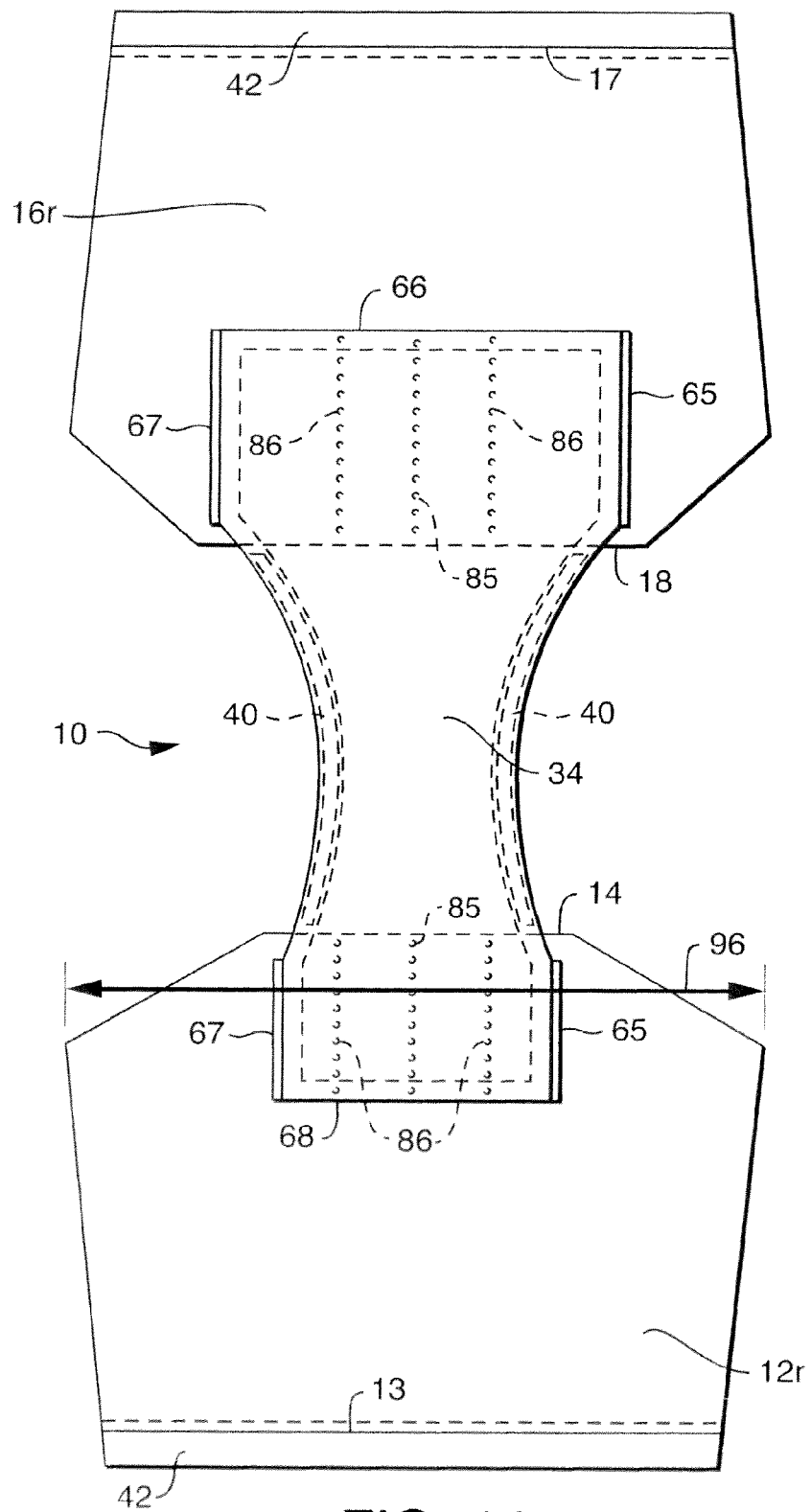
FIG. 11 representatively illustrates a plan view of still another embodiment of a disposable absorbent garment incorporating principles of the garment aspect of the present invention, shown in a relaxed and laid-flat condition, prior to the joining of the front and back waist regions, and showing the surface of the article that faces toward the wearer when the article is worn.

The absorbent assembly can in particular embodiments include a bodyside topsheet 34, a garment-side backsheet 36, and the absorbent core 26 can be sandwiched between the topsheet 34 and the backsheet 36, as representatively illustrated in FIGS. 4 and 5. The absorbent assembly can further include leg elastics 40, such as leg elastics 40 that are sandwiched between the topsheet 34 and the backsheet 36. In particular embodiments, the absorbent core 26 is composed of fiberized wood pulp and/or superabsorbent polymer, and the core 26 can optionally include upper and lower absorbent wrapsheets, such as tissue or nonwoven wrapsheets. An acquisition layer, not shown, can be optionally used, and can be sandwiched between the topsheet and the upper wrapsheet. An acquisition layer can function to rapidly absorb and temporarily retain body fluid, such as urine, before it can be absorbed into the absorbent core 26.

Figure 2B:
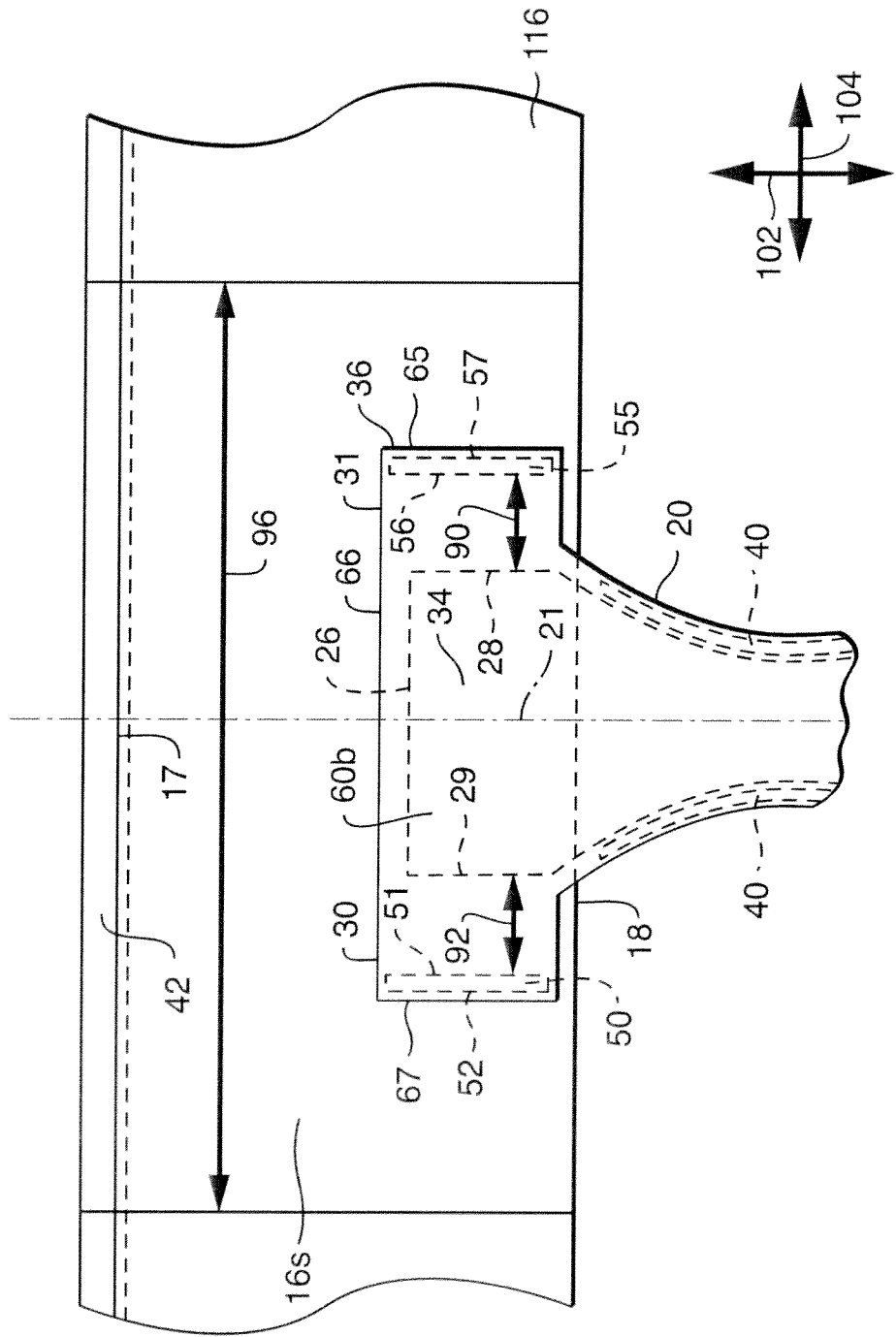
FIG. 2B shows an enlarged section of FIG. 2A.
Figure 3:
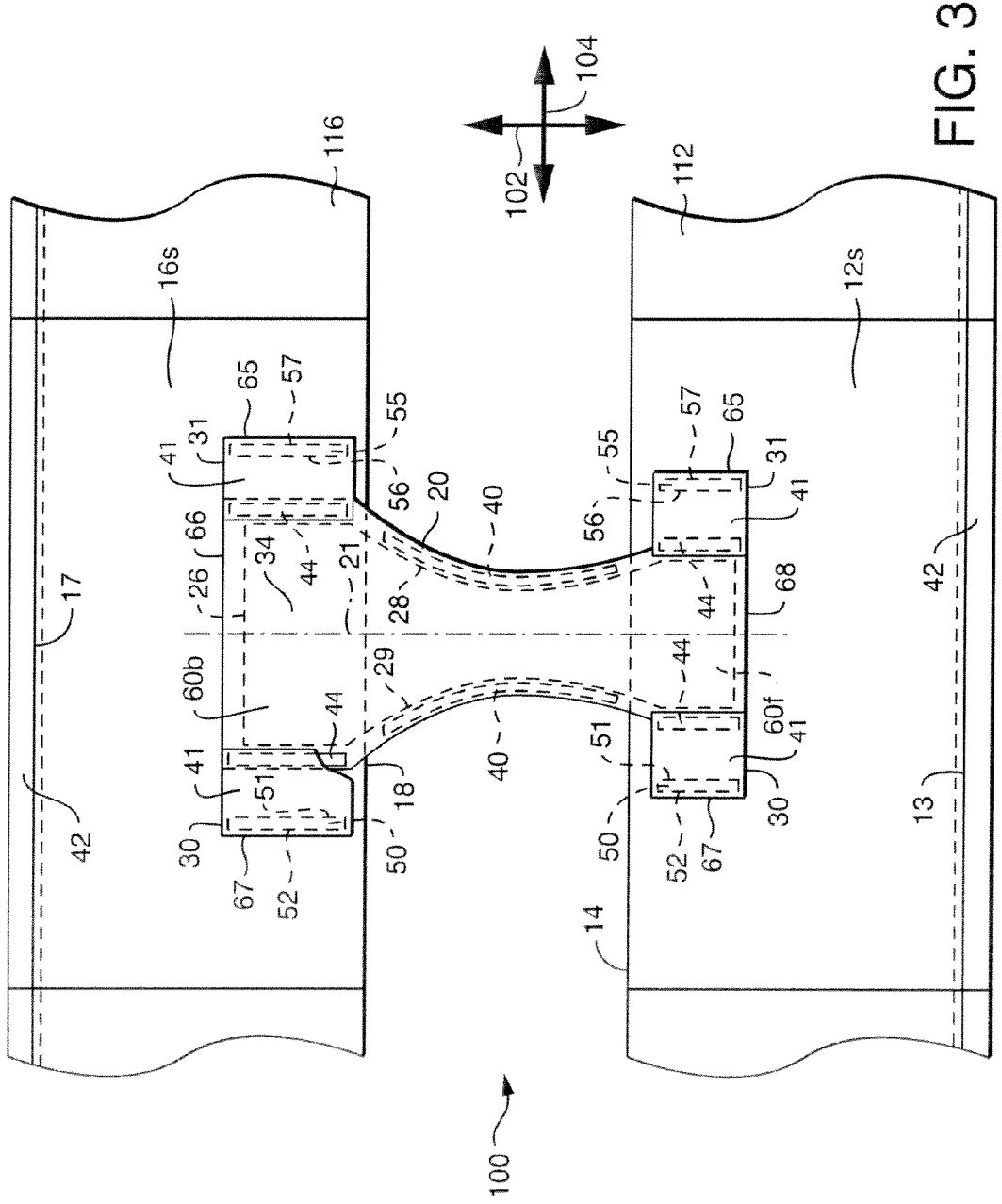
FIG. 3 representatively illustrates a plan view of another variant of a section of the manufacturing process of FIG. 1.

In particular embodiments, the side margins 30, 31 comprise an integral portion of the topsheet 34, of the backsheet 36, or, as representatively illustrated in FIGS. 2A, 2B and 5, of both the topsheet 34 and the backsheet 36. In a desirable embodiment, the topsheet 34 and the backsheet 36 are coextensive throughout the absorbent assembly 20. In other embodiments, such as that representatively illustrated in FIG. 3, the side margins 30, 31 can comprise separate components 41 connected to the topsheet 34 and/or backsheet 36, such as via bond lines 42. Bond lines 42 can be created, for example, via the use of adhesive, or via the use of ultrasonic, heat, and/or pressure energy. Separate components 41 used to at least in part define the side margins 30, 31 can be made of any suitable material, such as nonwoven or polymeric materials. Components 41 can be non-stretchable, stretchable, elastomeric, or other suitable configuration. Employing separate components 41 to at least in part define the side margins 30, 31 can in certain embodiments reduce the amount of trim waste created by the method 100.

The method further includes stretching each elastomeric body panel 12, 16 in the transverse direction 104 (which is also the machine direction in FIGS. 1-3) to define stretched elastomeric body panels 12s, 16s. The method further includes superposing the absorbent assembly 20 over the elastomeric body panel 16, such as superposing the absorbent assembly 20 over the stretched elastomeric body panel 12s and/or 16s. In the examples shown in FIGS. 1-3, a portion of the absorbent assembly 20 is superposed over the stretched elastomeric body panel 12s, and a portion of the absorbent assembly 20 is superposed over the stretched elastomeric body panel 16s. In certain embodiments, such as that representatively illustrated in FIG. 1, the method includes cutting the individual absorbent assemblies 20 from the supply 150 and rotating them 90 degrees at a cut-and-rotate station 152.

The method further includes attaching the first side margin 30 to the stretched elastomeric body panel 12s/16s along a first attachment region 50. In particular embodiments, the first attachment region 50 extends generally in the longitudinal direction 102. The first attachment region 50 defines a longitudinally extending first edge 51 and a longitudinally extending second edge 52. The longitudinally extending second edge 52 is disposed transversely outward from the longitudinally extending first edge 51. The first edge 51 of the first attachment region 50 is disposed transversely outward from the first core side edge 28. Adhesive, or ultrasonic, heat, or pressure energy, or other suitable technique, can be used to attach the first side margin 30 to the stretched elastomeric body panel 12s/16s. The attachment region 50 can be a continuous, uninterrupted bond or seam, or can be a discontinuous bond or seam having one or more gaps or breaks.

The method further includes attaching the second side margin 31 to the stretched elastomeric body panel 12s/16s along a second attachment region 55. In particular embodiments, the second attachment region 55 extends generally in the longitudinal direction 102. The second attachment region 55 defines a longitudinally extending first edge 56 and a longitudinally extending second edge 57. The longitudinally extending second edge 57 is disposed transversely outward from the longitudinally extending first edge 56. The first edge 56 of the second attachment region 55 is disposed transversely outward from the second core side edge 29. Adhesive, or ultrasonic, heat, or pressure energy, or other suitable technique, can be used to attach the second side margin 31 to the stretched elastomeric body panel 12s/16s. The attachment region 55 can be a continuous, uninterrupted bond or seam, or can be a discontinuous bond or seam having one or more gaps or breaks.

The absorbent assembly defines a center region 60 that extends transversely from the first edge 51 of the first attachment region 50 to the first edge 56 of the second attachment region 55. The center region 60 extends longitudinally from the first absorbent assembly end edge 66 to the crotch edge 14. The center region 60 of the absorbent assembly 20 is minimally attached to the stretched elastomeric body panel 12s/16s. "Minimally attached" as used herein with reference to the center region 60 of the absorbent assembly 20 means that no more than 25% of the surface area of the center region 60 (that is, the area of the surface of a center region that faces the elastomeric body panel) is attached to the elastomeric body panel 12s/16s. Note that the embodiments depicted in FIGS. 1 and 2 include two center regions 60—one at each longitudinal end of the absorbent assembly 20. In such an embodiment, "minimally attached" with reference to either center region 60 of the absorbent assembly 20 means that no more than 25% of the surface area of the front center region 60f is attached to the stretched elastomeric body panel 12s, and that no more than 25% of the surface area of the back center region 60b is attached to the stretched elastomeric body panel 16s. As used herein, "minimally attached" can mean that zero percent (0%) of the area of a center region 60 is attached to the underlying elastomeric body panel. In particular embodiments, the center region 60 is not attached at all to the stretched elastomeric body panel 12s (that is, the percentage of the area of the center region 60 that is attached to the elastomeric body panel 12s is zero). Similarly, in particular embodiments, the center region 60 is not attached at all to the stretched elastomeric body panel 16s (that is, the percentage of the area of the center region 60 that is attached to the elastomeric body panel 16s is zero). Stated another way, in particular embodiments, the entire area of the center region 60 is unattached to the stretched elastomeric body panel over which it is superposed.

The method further includes relaxing the stretched elastomeric body panel 12s, 16s to define a relaxed elastomeric body panel 12r, 16r. The method further includes transversely folding the first side margin 30 to create at least two longitudinally extending folds 70, 72 in the first side margin 30. In particular embodiments, the relaxing of the elastomeric body panel 12/16 produce the two folds 70, 72. The folds 70, 72 define a "z-folded" cross section in the first side margin 30, as representatively illustrated in FIGS. 4, 8, and 9. The method further includes transversely folding the second side margin 31 to create at least two longitudinally extending folds 74, 76 in the second side margin 31. In particular embodiments, the relaxing of the elastomeric body panel 12/16 produce the two folds 74, 76. The folds 74, 76 define a "z-folded" cross section in the second side margin 31, as representatively illustrated in FIG. 8.

Without wishing to be bound by any particular mechanism, it has been discovered that in embodiments in which the center region 60 of the absorbent assembly 20 is minimally attached to the stretched elastomeric body panel 12s/16s, that, when the stretched elastomeric body panel 12s/16s is relaxed, the center portion 60 of the absorbent assembly 20 is subjected to minimal or no gathering or bunching forces. Generally speaking, the lower the percentage of the area of the center portion 60 that is attached to the elastomeric body panel 12/16, the less bunching/gathering of the center portion 60. As described above, this is advantageous, because gathered, bunched absorbent assemblies tend to increase the bulkiness of the product during wear, and also can degrade the aesthetics of the product pre-use. It is instead preferable that the garment appear flat and smooth, akin to real, cloth underwear. This is because, it is hypothesized in particular embodiments, the portion of the elastomeric body panel 12/16 that is positioned transversely between the longitudinally extending first edge 51 and the longitudinally extending first edge 56 is substantially free to extend and retract, relatively unrestricted by the center portion 60 of the absorbent assembly 20.

In particular embodiments, the method includes attaching at least 2% and at most 25% of the area of the center region 60 of the absorbent assembly 20 to one or both stretched elastomeric body panels 12s/16s. Adhesive, or ultrasonic, heat, or pressure energy, or other suitable technique, can be used to attach the center region 60 to a stretched elastomeric body panel. In alternative embodiments, the method includes attaching at least 2% and at most 25% of the area of the center region 60 of the absorbent assembly 20 to one or both relaxed elastomeric body panels 12r/16r.

In a particular embodiment, the method includes attaching the center region 60 of the absorbent assembly 20 to an elastomeric body panel, such as a stretched elastomeric body panel 12s and/or 16s, along a middle attachment region 85. In such an embodiment, the middle attachment region 85 extends generally in the longitudinal direction 102. In particular embodiments, such as that representatively illustrated in FIGS. 10 and 11, a transverse centerline of the middle attachment region 85 is positioned approximately midway between the first assembly side edge 65 and the second assembly side edge 67. Employing a middle attachment region in this manner can assist in preventing the middle portion 60 of the absorbent assembly 20 from pulling away from and forming a gap with respect to the elastomeric body panel 12/16 before and/or during use of the garment, but at the same time resulting in minimal bunching/gathering of the center portion 60 upon relaxation of the elastomeric body panel, due to the transversely central and relatively neutral location of the middle attachment region 85. In particular embodiments, the method can further include attaching the center region 60 of the absorbent assembly 20 to an elastomeric body panel 12/16 along one or more additional attachment regions 86. Adhesive, or ultrasonic, heat, or pressure energy, or other suitable technique, can be used to attach the center region 60 to the stretched elastomeric body panel 12s/16s. The attachment regions 85 or 86 can constitute continuous, uninterrupted bonds or seams, or can constitute discontinuous bonds or seams having one or more gaps or breaks.

In particular embodiments, the method includes attaching the center region 60 of the absorbent assembly 20 to the stretched elastomeric body panel 12s/16s along a top attachment region 88. In such an embodiment, as is representatively illustrated in FIG. 9, the top attachment region 88 extends generally in the transverse direction 104 along the first assembly end edge 66 or along the second assembly end edge 68, as the case may be. Employing a top attachment region 88 in this manner can assist in preventing the middle portion 60 of the absorbent assembly 20 from pulling away from and forming a gap with respect to the elastomeric body panel 12/16 before and/or during use of the garment, but at the same time result in minimal bunching/gathering of the center portion 60 upon relaxation of the elastomeric body panel 12/16, due to the longitudinally marginal location of the top attachment region 88 relative to the center portion 60 as a whole. Adhesive, or ultrasonic, heat, or pressure energy, or other suitable technique, can be used to attach the center region 60 to the stretched elastomeric body panel 12s/16s. The attachment region 88 can constitute a continuous, uninterrupted bond or seam, or can constitute a discontinuous bond or seam having one or more gaps or breaks.

In particular embodiments, the first edge 51 and the first core side edge 28 define therebetween a first distance 90. The first edge 56 and the second core side edge 29 define therebetween a second distance 92. A stretched elastomeric stretch panel 12s/16s defines an in-process stretched length 94, and a relaxed elastomeric stretched panel 12r/16r defines a relaxed length 96. The difference between the stretched length 94 and the relaxed length 96 is the stretched distance. In particular embodiments of the method aspect of the present invention, the first distance 90 is at least 30% of, more particularly at least 40% of, and most particularly at least 50% of the stretched distance. Similarly, the second distance 92 is in particular embodiments at least 30% of, more particularly at least 40% of, and most particularly at least 50% of the stretched distance.

The method can optionally also include removing central portions 183 of the front panel web 112 and/or removing central portions 187 of the back panel web 116, such as via cutter unit 181, to define shaped front panel web leg edges 184 and/or shaped back leg edges 188. The method 100 can optionally include providing a front elastic waistband web 130 and a back elastic waistband web 140, such as via roll supplies 131 and 141 respectively. For example, the method can further include connecting a front elastic waistband web 130 proximate the front waist edge 13 at a front waistband attachment station 132, and connecting the back elastic waistband web 140 proximate the back waist edge 17 at a back waistband attachment station. The method optionally further comprises folding the garment web 190 (such as at folding station 154) along a longitudinally extending centerline 106 that extends in the transverse (machine) direction 104, such that the front waist edge 13 is brought into close proximity with the back waist edge 17. The method can further include attaching the front elastomeric body panel web 112 to the back elastomeric body panel web 116 (such as at seaming station 156) to create a series of garment side seam bonds 46 spaced apart in the machine direction. Finally, the method can include cutting the garment web 190 (such as at cutting station 168) at a series of cut locations 170 spaced apart in the machine direction to create the plurality of disposable absorbent garments 10. The garment side seam bonds 160 and the waistband side seam bonds 162 can be formed at the same seaming station (as depicted) or at separate seaming stations. The seaming operation can be performed along with the final cutting operation at a single station, or at a separate station (as depicted).

In another aspect, the present invention relates to a garment 10. The garment 10 defines a longitudinal direction 102 and a transverse direction 104 perpendicular to the longitudinal direction 102. As used with respect to an individual garment, "longitudinal" and "transverse" have their customary meaning, as indicated by the longitudinal and transverse axes depicted in FIGS. 9-11. With the garment 10 in a laid-flat condition, prior to the joining of the front and back waist regions via side seams 46, the longitudinal axis 102 of a garment lies in the plane of the article and is generally parallel to a vertical plane that bisects a standing wearer into left and right body halves when the article is worn. The transverse axis 104 lies in the plane of the article generally perpendicular to the longitudinal axis.

The garment 10 comprises at least one elastomeric body panel 12/16 having a construction as described above in conjunction with the method aspect. The garment comprises an absorbent assembly 20 as described above. The absorbent assembly 20 is at least partially superposed over the elastomeric body panel 12/16. The first side margin 30 is attached to the elastomeric body panel 12/16 along a first attachment region 50 as described above, and the second side margin 31 is attached to the elastomeric body panel 12/16 along a second attachment region 55 as described above. The absorbent assembly 20 further defines a center region 60 as described above. The center region 60 of the absorbent assembly 20 is minimally attached to the elastomeric body panel 12/16 in any of the configurations described above. The first side margin 30 defines at least two longitudinally extending fold lines 70, 72, such that the first side margin defines a z-folded cross section, and the second side margin 31 defines at least two longitudinally extending fold lines 74, 76, such that the second side margin 31 also defines a z-folded cross section. In certain embodiments, at least 2% and at most 25% of the area of the center region 60 of the absorbent assembly 20 is attached to the elastomeric body panel 12/16. In certain embodiments, the center region 60 of the absorbent assembly 20 is attached to the elastomeric body panel 12/16 along a middle attachment region 85, the middle attachment region 85 extending generally in the longitudinal direction and positioned approximately midway between the first assembly side edge 65 and the second assembly side edge 67. In certain embodiments, the center region 60 of the absorbent assembly 20 is attached to the elastomeric body panel 12/16 along a top attachment region 88. In such an embodiment, the top attachment region 88 extends generally in the transverse direction 104 along the first assembly end edge 66 or along the second assembly end edge 68, as the case may be. In other embodiments, the entire area of the center region 60 is unattached to the elastomeric body panel 12/16.

It will be appreciated that details of the foregoing embodiments, given for purposes of illustration, are not to be construed as limiting the scope of this invention. Although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. In a method of making a disposable absorbent garment, the method defining a longitudinal direction and a transverse direction perpendicular to the longitudinal direction, the method comprising:

providing an elastomeric body panel that defines a waist edge and a crotch edge longitudinally opposite the waist edge;

providing an absorbent assembly that defines transversely opposed first and second assembly side edges and that defines longitudinally opposed first and second assembly end edges, the absorbent assembly comprising an absorbent core, the absorbent core having transversely opposed first and second core side edges, the absorbent assembly further comprising a first side margin that extends transversely outward from the first core side edge to the first assembly side edge, the absorbent assembly further comprising a second side margin that extends transversely outward from the second core side edge to the second assembly side edge;

stretching the elastomeric body panel in the transverse direction to define a stretched elastomeric body panel;

superposing the absorbent assembly over the elastomeric body panel;

attaching the first side margin to the stretched elastomeric body panel along a first attachment region, the first attachment region extending generally in the longitudinal direction, the first attachment region defining a longitudinally extending first edge and a longitudinally extending second edge disposed transversely outward from the longitudinally extending first edge, wherein the first edge of the first attachment region is disposed transversely outward from the first core side edge;

attaching the second side margin to the stretched elastomeric body panel along a second attachment region, the second attachment region extending generally in the longitudinal direction, the second attachment region defining a longitudinally extending first edge and a longitudinally extending second edge disposed transversely outward from the longitudinally extending first edge, wherein the first edge of the second attachment region is disposed transversely outward from the second core side edge;

the absorbent assembly further defining a center region that extends transversely from the first edge of the first attachment region to the first edge of the second attachment region and that extends longitudinally from the first assembly end edge to the crotch edge, wherein said center region of the absorbent assembly is minimally attached to the stretched elastomeric body panel; and relaxing the elastomeric body panel to define a relaxed elastomeric body panel and to create at least two longitudinally extending fold lines in the first side margin and to create at least two longitudinally extending fold lines in the second side margin.

2. The method of claim 1, wherein transversely folding the first side margin imparts a z-folded cross section to the first side margin, and further wherein transversely folding the second side margin imparts a z-folded cross section to the second side margin.

3. The method of claim 1, further comprising attaching at least 2% and at most 25% of the area of the center region of the absorbent assembly to the stretched elastomeric body panel.

4. The method of claim 1, further comprising attaching the center region of the absorbent assembly to the stretched elastomeric body panel along a middle attachment region, the middle attachment region extending generally in the longitudinal direction, wherein a transverse centerline of the middle attachment region is positioned approximately midway between the first assembly side edge and the second assembly side edge.

5. The method of claim 1, further comprising attaching the center region of the absorbent assembly to the stretched elastomeric body panel along a top attachment region, the top attachment region extending generally in the transverse direction along the first assembly end edge.

6. The method of claim 1, further wherein the entire area of the center region is unattached to the stretched elastomeric body panel.

* * * * *